(12) United States Patent
Hatanaka et al.

(10) Patent No.: US 12,290,653 B2
(45) Date of Patent: May 6, 2025

(54) MICRONEEDLE SHEET PRODUCTION METHOD AND MICRONEEDLE SHEET

(71) Applicant: HISAMITSU PHARMACEUTICAL CO., INC., Tosu (JP)

(72) Inventors: Eisuke Hatanaka, Tsukuba (JP); Kazuki Kuriyama, Tsukuba (JP); Naoki Yamamoto, Tsukuba (JP)

(73) Assignee: HISAMITSU PHARMACEUTICAL CO., INC., Tosu (JP)

( * ) Notice: Subject to any disclaimer, the term of this patent is extended or adjusted under 35 U.S.C. 154(b) by 1183 days.

(21) Appl. No.: 16/973,553

(22) PCT Filed: Jul. 11, 2019

(86) PCT No.: PCT/JP2019/027588
§ 371 (c)(1),
(2) Date: Dec. 9, 2020

(87) PCT Pub. No.: WO2020/017436
PCT Pub. Date: Jan. 23, 2020

(65) Prior Publication Data
US 2021/0244925 A1    Aug. 12, 2021

(30) Foreign Application Priority Data
Jul. 19, 2018   (JP) .................................. 2018-135912

(51) Int. Cl.
*A61M 37/00*    (2006.01)
(52) U.S. Cl.
CPC . *A61M 37/0015* (2013.01); *A61M 2037/0023* (2013.01); *A61M 2037/0053* (2013.01)

(58) Field of Classification Search
CPC . A61K 9/0021; A61K 47/32; A61M 37/0015; A61M 2037/0053; A61M 2037/0023; A61M 2037/0061
See application file for complete search history.

(56) References Cited

U.S. PATENT DOCUMENTS

| | | |
|---|---|---|
| 2011/0034860 A1 | 2/2011 | Melsheimer |
| 2017/0239458 A1 | 8/2017 | Kato et al. |

FOREIGN PATENT DOCUMENTS

| | | |
|---|---|---|
| CN | 1691970 A | 11/2005 |
| CN | 101687090 A | 3/2010 |
| CN | 103623499 A | 3/2014 |
| CN | 104379209 A | 2/2015 |

(Continued)

OTHER PUBLICATIONS

Extended European Search Report dated May 11, 2022 corresponding to application No. 19838833.2-1122.

(Continued)

*Primary Examiner* — Monica A Huson
(74) *Attorney, Agent, or Firm* — Nath, Goldberg & Meyer; Joshua B. Goldberg (57) ABSTRACT

A method of producing a microneedle sheet according to an embodiment includes: preparing a sheet having a first surface and a second surface; making a first cut in a range from the first surface to the second surface of the sheet to form a first outer edge that defines a tip end of the microneedle; and making, after forming the first outer edge, a second cut in a range from the first surface to the second surface of the sheet to form a second outer edge that defines the tip end of the microneedle, thereby forming the tip end of the microneedle.

7 Claims, 8 Drawing Sheets

(56) References Cited

FOREIGN PATENT DOCUMENTS

| | | |
|---|---|---|
| CN | 104780966 A | 7/2015 |
| CN | 106413797 A | 2/2017 |
| CN | 107405477 A | 11/2017 |
| CN | 110076528 A | 8/2019 |
| CN | 110153651 A | 8/2019 |
| JP | 2008284318 A | 11/2008 |
| JP | 2014113318 A | 6/2014 |
| JP | 2015-151380 A | 8/2015 |
| JP | 6064012 B1 | 1/2017 |
| JP | 201738904 A | 2/2017 |
| JP | 2017038903 A | 2/2017 |
| WO | 2013187392 A1 | 12/2013 |
| WO | 2016147476 A1 | 9/2016 |
| WO | 2017002466 A1 | 1/2017 |
| WO | 2017030012 A1 | 2/2017 |
| WO | 2018026955 A1 | 2/2018 |
| WO | 2018043574 A1 | 3/2018 |

OTHER PUBLICATIONS

Japanese Office Action dated Jun. 22, 2021 corresponding to application No. P2020-531278.
Machine Translation of First Office Action issued for Chinese Application No. 201980040225.0, dated Jan. 29, 2022.
International Search Report dated Aug. 27, 2019 corresponding to application No. PCT/JP2019/027588.
Chinese Office Action dated Jul. 15, 2022 corresponding to application No. 201980040225.0.
International Preliminary Report on Patentability(IPRP) dated Jan. 28, 2021 corresponding to application No. PCT/JP2019/027588.
Chinese Office Action dated Jan. 29, 2022 corresponding to application No. 201980040225.0.
Pang, Qi-shou, et al. "Corner Protection in Wire Cut Electrical Discharge Machining"; Journal of Jiangxi University of Science and Technology; vol. 31, No. 3; Jun. 2010.

MICRONEEDLE SHEET PRODUCTION METHOD AND MICRONEEDLE SHEET

This is a National Phase Application filed under 35 U.S.C. 371 as a national stage of PCT/JP2019/027588, filed Jul. 11, 2019, an application claiming the benefit of Japanese Application No. 2018-135912, filed Jul. 19, 2018, the content of each of which is hereby incorporated by reference in its entirety.

TECHNICAL FIELD

An aspect of the present invention relates to a microneedle sheet and a method of producing the same.

BACKGROUND ART

Microneedle sheets used for assisting in transdermal administration of active components are known. The microneedle sheet includes one or more (for example, a large number of) microneedles inserted into the skin in use. For example, Patent Literature 1 describes a microneedle sheet configured such that when the sheet is bent, microneedles are raised from the surface, and the raised microneedles are inserted into the skin.

CITATION LIST

Patent Literature

Patent Literature 1: WO 2013/187392

SUMMARY OF INVENTION

Technical Problem

It is preferable that the tip ends of microneedles are sharp for puncturing. There is therefore a need for a method of producing a microneedle sheet for producing microneedles with sharp tip ends.

Solution to Problem

A method of producing a microneedle sheet according to an aspect of the present invention is a method of producing a microneedle sheet having at least one microneedle. The method includes: preparing a sheet having a first surface and a second surface; making a first cut in a range from the first surface to the second surface of the sheet to form a first outer edge that defines a tip end of the microneedle; and making, after forming the first outer edge, a second cut in a range from the first surface to the second surface of the sheet to form a second outer edge that defines the tip end of the microneedle, thereby forming the tip end of the microneedle.

In such an aspect, two outer edges (the first outer edge and the second outer edge) that define the tip end of the microneedle are not formed at one time but are formed separately by making cuts in the sheet in two stages. This technique can sharpen the tip end of the microneedle.

Advantageous Effects of Invention

According to an aspect of the present invention, microneedles with sharp tip ends can be produced.

DESCRIPTION OF EMBODIMENTS

Embodiments of the present invention will be described in detail below with reference to the accompanying drawings. In a description of the drawings, the same or equivalent elements are denoted by the same reference signs, and an overlapping description will be omitted.

[Structure of Microneedle Sheet]

Figure 1:
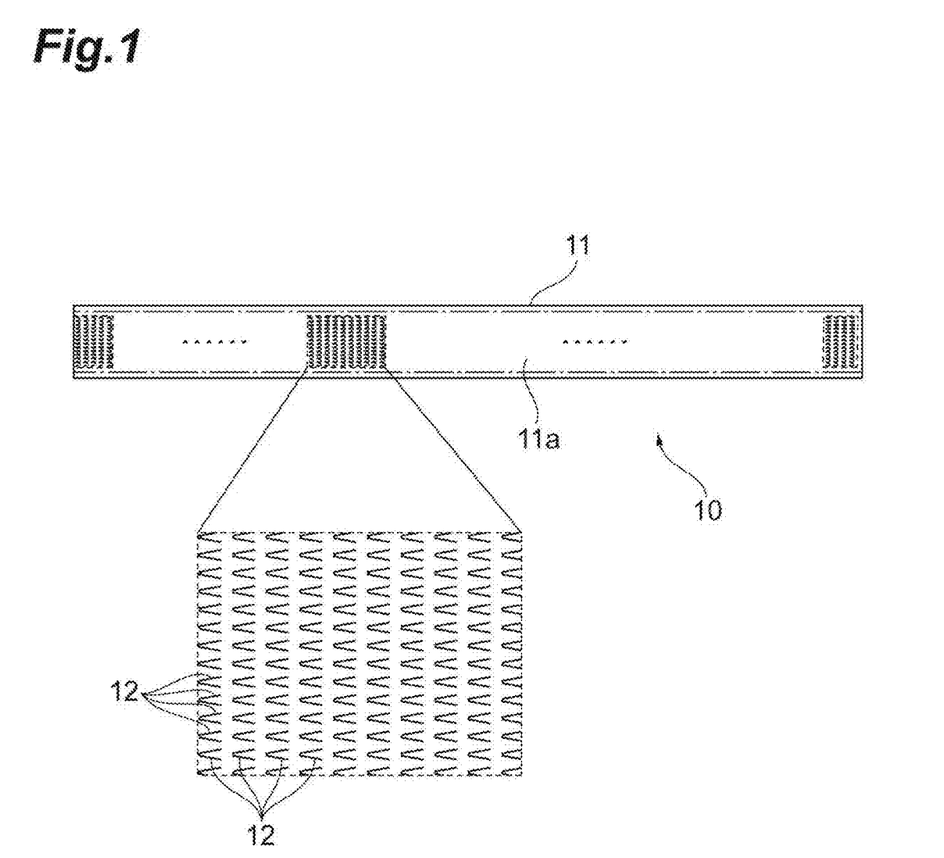
FIG. 1 is a plan view illustrating an example of a microneedle sheet according to an embodiment.
Figure 2:
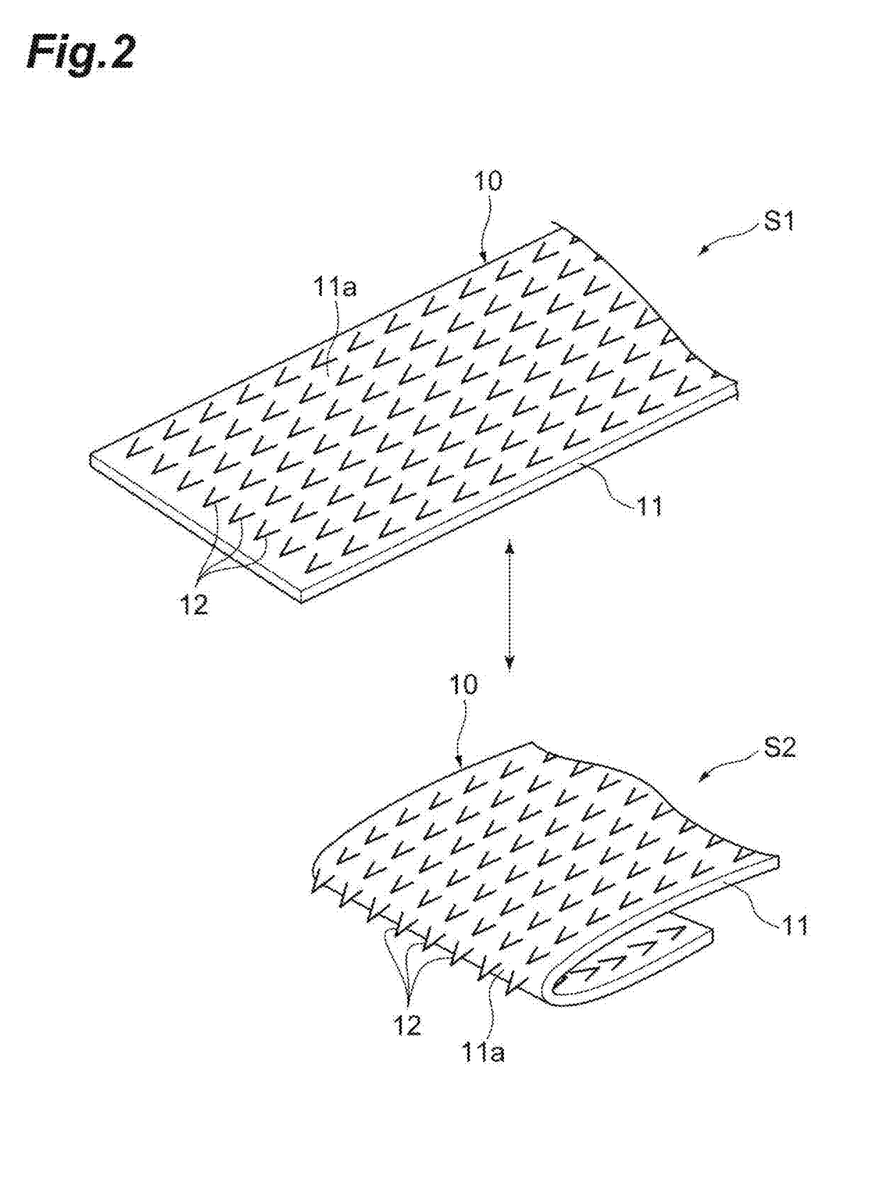
FIG. 2 is a diagram illustrating two states of the microneedle sheet according to the embodiment.
Figure 3:
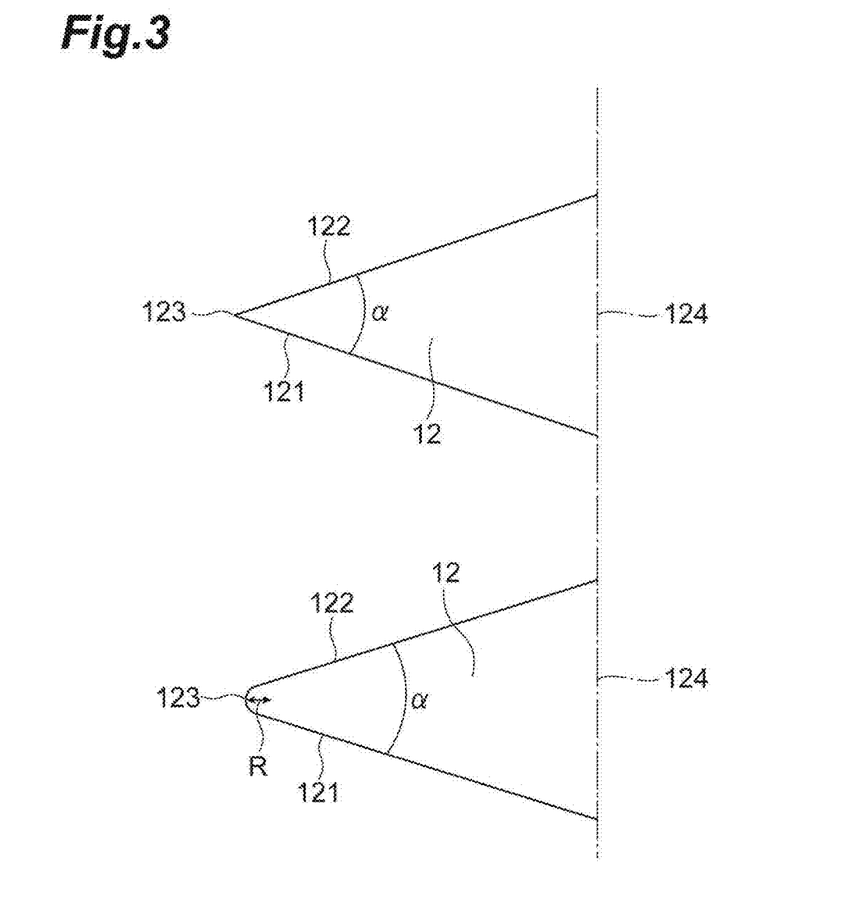
FIG. 3 is a diagram illustrating an example of microneedles.

Referring to FIG. 1 to FIG. 3, a structure of a microneedle sheet 10 according to an embodiment is described. FIG. 1 is a plan view illustrating an example of the microneedle sheet 10 according to the embodiment. FIG. 2 is a diagram illustrating two states of the microneedle sheet 10. FIG. 3 is a diagram illustrating an example of microneedles 12.

The microneedle sheet 10 is an instrument for administering any active component (for example, drug) into a living body through the skin. In the example in FIG. 1, the microneedle sheet 10 has a strip shape (elongated rectangular shape). The microneedle sheet 10 has a thin plate-shaped sheet body 11 and one or more microneedles 12 formed on the sheet body 11. In the present embodiment, a direction along the long side is referred to as the longitudinal direction of the microneedle sheet 10 (or the sheet body 11), and a direction along the short side (direction orthogonal to the longitudinal direction) is referred to as the width direction of the microneedle sheet 10 (or the sheet body 11). The direction orthogonal to both of the longitudinal direction and the width direction is referred to as the thickness direction of the microneedle sheet 10 (or the sheet body 11).

Each individual microneedle 12 is a portion inserted into the skin of a living body in use of the microneedle sheet 10. For example, a plurality of microneedles 12 may be formed such that two or more microneedles 12 are aligned in each of the longitudinal direction and the width direction of the sheet body 11.

At a point of time when the microneedle sheet 10 is provided (that is, at a point of time before use), the microneedle sheet 10 is not bent and is straight. Hereinafter, this state may be referred to as "first state". On the other hand, when the microneedle sheet 10 is used, at least a part of the sheet body 11 of the microneedle sheet 10 is bent such that a curved surface is formed in a direction intersecting the orientation of the tip ends of the microneedles 12. Hereinafter, this state may be referred to as "second state". For example, the sheet body 11 is bent such that a curved surface is formed along a direction orthogonal to or substantially orthogonal to the orientation of the tip ends of the microneedles 12. As illustrated in FIG. 2, the microneedle sheet 10 can change from the first state S1 to the second state S2 and can return from the second state S2 to the first state S1. In the second state S2 illustrated in FIG. 2, the sheet body 11 is bent such that a curved surface is formed along a direction orthogonal to the orientation of the tip ends of the microneedles 12.

"The tip end of the microneedle" refers to a region on the tip end side of the microneedle. More specifically, "the tip end of the microneedle" is a region including the apex (theoretically, a portion that first comes into contact with the skin in puncturing) of the microneedle and a portion of the microneedle near the apex.

In the first state S1, each microneedle 12 is not raised from a main surface 11a of the sheet body 11 and is laid along the main surface 11a. In other words, the tip end of each of the microneedles 12 is oriented toward one end (the left direction in FIG. 1) of the sheet body 11 in the longitudinal direction. In other words, the angle formed between each microneedle 12 and the sheet body 11 (main surface 11a) is 0° or substantially 0°. The orientation of some of the microneedles 12 may differ from the orientation of other microneedles 12.

The second state S2 is produced when the sheet body 11 advancing in the direction in which the tip ends of the microneedles 12 are oriented is bent into an acute angle. In this second state S2, at least one microneedle 12 positioned at a bent portion of the sheet body 11 is raised from the main surface 11a. The angle formed between the microneedle 12 positioned at a first portion of the microneedle sheet 10 and the main surface 11a is changed (increased) by bending the first portion. Specifically, the angle increases from 0° or substantially 0° to a larger value (for example, any value between 10 to 90°). When the raised microneedle 12 is advanced into the skin as it is, the microneedle 12 can be inserted into the skin.

When the first portion being bent returns to the original state (that is, a straight state), the angle formed between the microneedle 12 positioned at the first portion and the main surface 11a changes (decreases). For example, the angle becomes 0° or substantially 0° again. However, as a matter of course, the microneedle 12 inserted into the skin is still raised from the main surface 11a even when the section of the sheet body 11 where the inserted microneedle 12 is located becomes straight.

In the present embodiment, the microneedle 12 has a triangular shape, but the shape is not limited. In the example in FIG. 1, the size and the orientation of the microneedles 12 are uniform. However, at least one of the size and the orientation is not necessarily uniform. The distribution of the microneedles 12 in the microneedle sheet 10 may or may not be uniform. For example, when the microneedle sheet 10 is viewed along the longitudinal direction, a plurality of microneedles 12 may be formed on the sheet body 11 such that a region including one or more microneedles 12 and a region including no microneedles 12 are alternately present.

The dimensions of the microneedle sheet 10 are not limited. Specifically, the lower limit of the thickness may be 5 µm, 10 µm, 20 µm, 30 µm, 40 µm, or 50 µm, and the upper limit of the thickness may be 1000 µm, 500 µm, 300 µm, 200 µm, 150 µm, 100 µm, 90 µm, 80 µm, 70 µm, 60 µm, or 50 µm. This thickness is the thickness of the sheet body 11 and also the thickness of the microneedles 12. The lower limit of the thickness of the microneedle sheet 10 may therefore be determined in consideration of the strength of the microneedles 12 that punctures the skin. The upper limit of the thickness may be determined in consideration of the flexibility of the sheet body 11, the puncture characteristics of the microneedles 12, and so on. The lower limit of the length of the microneedle sheet 10 may be 0.1 cm or 1 cm, and the upper limit of the length may be 50 cm or 20 cm. The lower limit of the width of the microneedle sheet 10 may be 0.1 cm or 1 cm, and the upper limit of the width may be 60 cm or 30 cm. The lower limits of the length and the width of the microneedle sheet 10 may be determined in consideration of the dose of an active component. The upper limits of the length and the width may be determined in consideration of the size of a living body.

As illustrated in FIG. 3, the microneedle 12 is sharp for the purpose of puncturing. The tip end of the microneedle 12 is defined with a first outer edge 121 and a second outer edge 122. The first outer edge 121 is an outer edge extending from an apex 123 to a base 124. The second outer edge is an outer edge positioned on the opposite side to the first outer edge 121 with the apex 123 interposed and extending from the apex 123 to the base 124. In the present embodiment, the microneedle 12 has a triangular shape, and therefore the first outer edge 121 and the second outer edge 122 form the entire microneedle 12. However, since the shape of the microneedle is not limited as described above, the microneedle may be defined with the first outer edge, the second outer edge, and one or more additional outer edges. Thus, at least one of the first outer edge and the second outer edge does not necessarily reach the base (base 124, in FIG. 3) of the microneedle in some cases.

A sharp microneedle is a concept that includes a case where the tip end of the microneedle is rounded in an allowable range. For example, it can be said that the microneedle 12 is sharp as long as the radius of curvature R of the tip end of the microneedle 12 is 30 µm or less. The word "sharp" therefore may mean that the radius of curvature R of the tip end of the microneedle 12 is 30 µm or less. The smaller the radius of curvature R is, the sharper the microneedle 12 is. The radius of curvature may be zero. FIG. 3 illustrates the microneedle 12 having a radius of curvature R of zero and the microneedle 12 having a radius of curvature R larger than zero but being sharp. The radius of curvature R of the microneedle 12 finally obtained may be an error caused at a stage of forming the microneedle 12 or may be a value intentionally set at the designing stage of the microneedle sheet 10.

The angle (tip end angle) $\alpha$ of the tip end of the microneedle 12 illustrated in FIG. 3 may be 10° or more and less than 180°. The lower limit of the tip end angle $\alpha$ may be, for example, 10°, 20°, 25°, or 30°, and the upper limit value of the tip end angle $\alpha$ may be, for example, 150°, 120°, 90°, 80°, 70°, 60°, 50°, or 40°. When the first outer edge and the second outer edge are curved, the tip end angle $\alpha$ may be defined by the angle formed between a tangent to the first outer edge and a tangent to the second outer edge in the vicinity of the apex.

The lower limit of the height (length) of the microneedle 12 may be 10 µm, 100 µm, or 200 µm, and the upper limit of the height may be 10000 µm, 1000 µm, or 500 µm. The lower limit of the density of microneedles 12 may be 0.05 needle per $cm^2$ or 1 needle per $cm^2$, and the upper limit of the density may be 10000 needles per $cm^2$ or 5000 needles per $cm^2$. The lower limit of the density may be calculated in terms of the number of microneedles 12 and the area with which 1 mg of an active component can be administered. The upper limit of the density may be set by a limit value in consideration of the shape of the microneedles 12.

The microneedles 12 are formed by making cuts in a sheet (sheet body 11). The thickness of each individual microneedle 12 (the length along the thickness direction) is the same as the thickness of the sheet body 11.

A preparation process for an active component applied to the skin is not limited. For example, an active component may be contained in the microneedle sheet 10 itself (more specifically, in the microneedles 12 themselves) in advance. Alternatively, the microneedle sheet 10 itself may be coated with an active component in advance. Alternatively, an active component may be applied onto the skin before the microneedles 12 puncture the skin. Alternatively, an active component may be applied onto the skin after the microneedles 12 puncture the skin. When the microneedle sheet 10 is coated with an active component in advance, it is preferable that a coating liquid having a predetermined viscosity is applied to the entire sheet at a thickness as uniform as possible. The uniform application can be easily achieved because the tip ends of the microneedles 12 are oriented toward one end of the sheet body 11 (because the microneedles 12 are laid along the main surface 11a). The coating may be performed using the principle of screen printing or may be performed by any other methods. An active component can be contained in the microneedle sheet 10 itself, for example, when a biodegradable sheet or a sheet fabricated using a water-soluble polymer is used.

The microneedle sheet 10 may be provided in such a manner that the main surface 11a is protected by a peel-off liner. Examples of the material of the peel-off liner include plastics such as PET. However, the material is not limited and, for example, metals or other kinds of resins may be used. When the microneedle sheet 10 is protected by a peel-off liner, the microneedle sheet 10 is fixed or temporarily attached to one surface of the peel-off liner by a tape or an adhesive.

The microneedles 12 are laid along the main surface 11a of the sheet body 11 before being bent. There is therefore no concern that the microneedles 12 are touched or caught by other objects (for example, the user's skin or clothes) at a stage before the microneedle sheet 10 is actually used. Consequently, the safety in handling the microneedles 12 can be ensured. For example, the user can safely perform storage, transportation, and preparation before use of the microneedle sheet 10.

[Method of Producing Microneedle Sheet]

Figure 4:
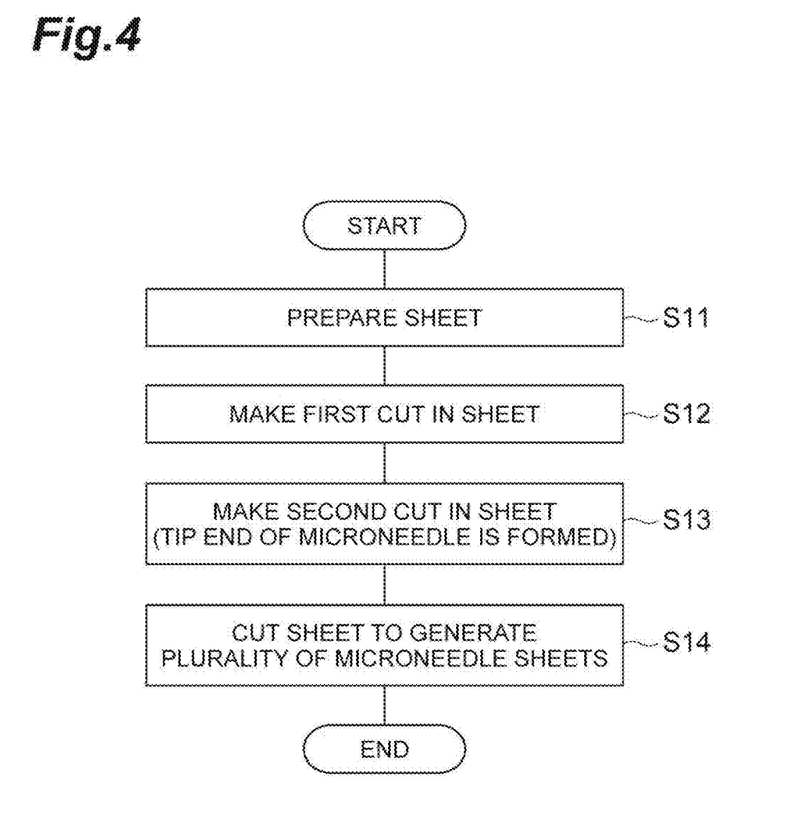
FIG. 4 is a flowchart illustrating a method of producing a microneedle sheet according to the embodiment.
Figure 5:
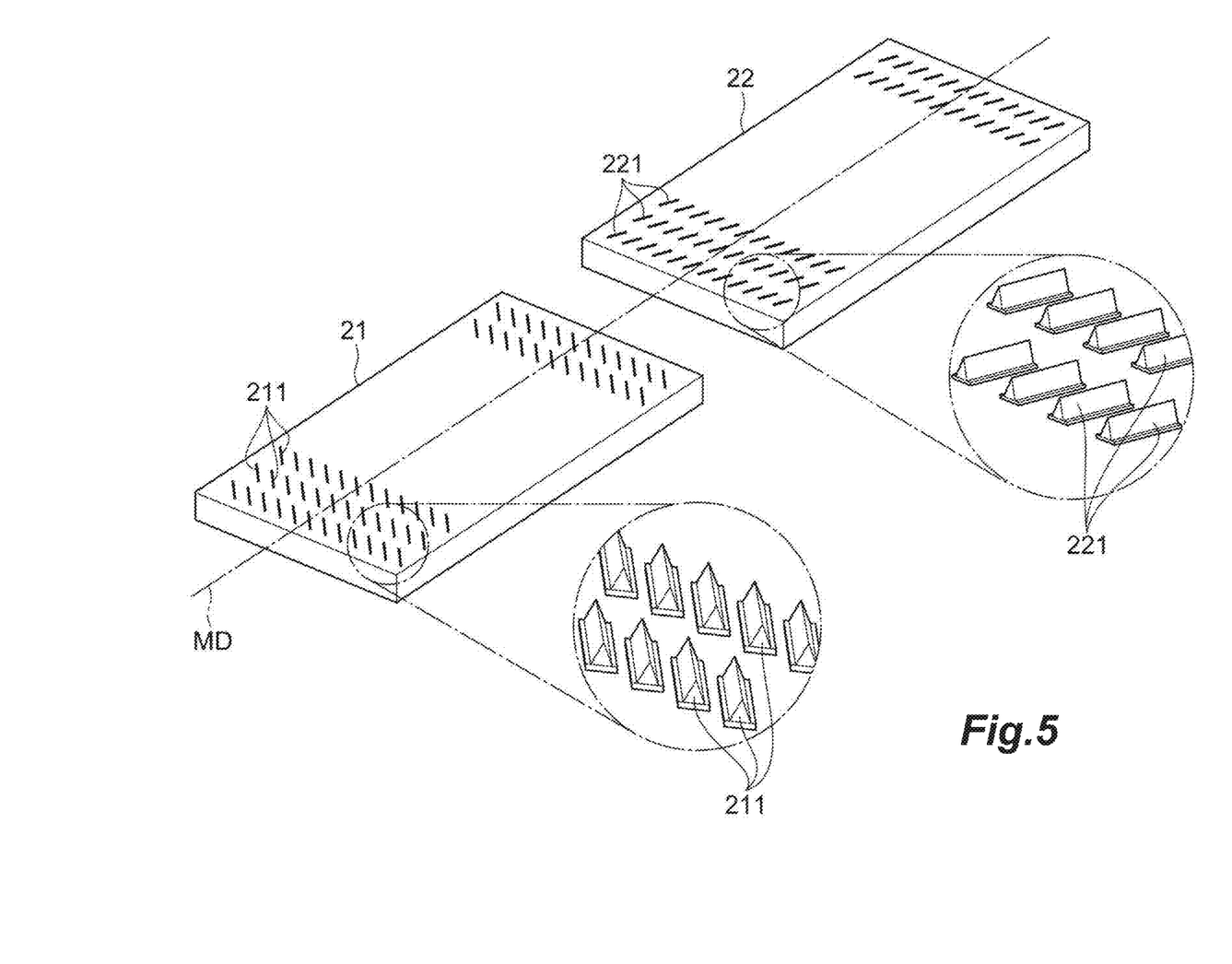
FIG. 5 is a diagram illustrating an example of cutting dies used in the method of producing a microneedle sheet according to the embodiment.
Figure 6:
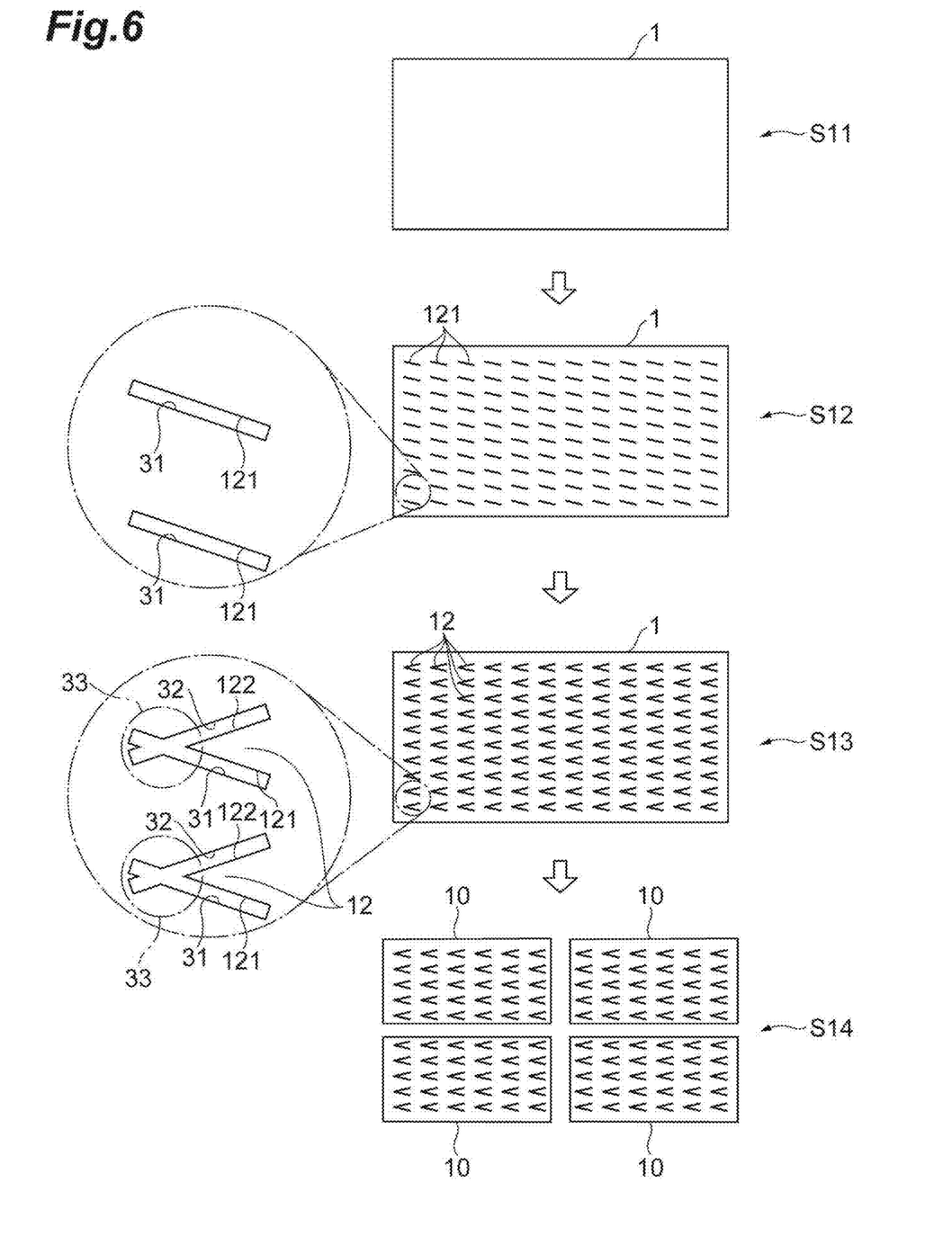
FIG. 6 is a diagram illustrating an example of the method of producing a microneedle sheet according to the embodiment.

Referring to FIG. 4 to FIG. 6, a method of producing a microneedle sheet according to the embodiment is described. FIG. 4 is a flowchart illustrating an example of the production method. FIG. 5 is a diagram illustrating an example of cutting dies used in the production method. FIG. 6 is a diagram illustrating an example of the production method.

The microneedle sheet 10 can be obtained by making cuts in a sheet to form the microneedles 12. FIG. 4 illustrates an example of the procedure. As used herein, "to form the microneedle" refers to forming at least an outer edge that defines the tip end of the microneedle.

At step S11, a sheet having a first surface and a second surface is prepared (preparation step). The microneedles 12 are not yet formed in this sheet. The first surface refers to one surface of the sheet (a surface extending in both of the longitudinal direction and the width direction), and the second surface refers to a surface on the opposite side to the first surface. One of the first surface and the second surface of the sheet serves as the main surface 11a of the sheet body 11.

The material of the sheet is not limited. For example, the material may be any one of resins, water-soluble polymers, biodegradable materials, bioabsorbable materials, metals, or ceramics. More specific examples of the material include pullulan, sodium hyaluronate, hyaluronic acid, chondroitin sulfate sodium, chondroitin sulfate, carboxymethylcellulose sodium (CMC-Na), carboxymethylcellulose (CMC), polyvinyl alcohol (PVA), polyvinylpyrrolidone (PVP), gelatin, sodium alginate, alginic acid, hydroxypropyl methylcellulose (HPMC), hydroxypropyl cellulose (HPC), poly(lactic-co-glycolic acid) (PLGA), polylactic acid (PLA), starch, sacran, polyethylene terephthalate (PET), nylon, polyimide, polyetheretherketone (PEEK), and polyglutamic acid. Alternatively, the sheet may be fabricated by combining these materials.

As described above, the microneedle sheet 10 is obtained by making cuts in the sheet to form the microneedles 12. The material of the sheet therefore is also the material of the microneedle sheet 10 and the microneedles 12. The "material of the sheet" is a substance intentionally used by the producer to fabricate the microneedle sheet 10 and the microneedles 12. In the production process of the sheet or the microneedle sheet 10, a substance not selected as a material (for example, a minute amount of impurity) may be included unintentionally, or such an unintended substance is not always completely removed. The microneedle sheet 10 may ultimately include a substance not intended by the producer, in addition to a material intended by the producer.

At step S12, a first cut is made in a range from the first surface to the second surface of the sheet to form the first outer edge 121 that defines the tip end of the microneedle 12 (first incision step). That is, a first cut was made from the first surface to the second surface of the sheet to form the first outer edge 121. It should be noted that "to make a first cut in a range from the first surface to the second surface", that is, "to make a first cut from the first surface to the second surface" is not dependent on the direction of making a cut. The first cut therefore may be made from the first surface toward the second surface, or made from the second surface toward the first surface. Since the first cut is formed in a range from the first surface to the second surface, the first cut passes through the sheet in the thickness direction. A gap is therefore produced by the first cut in the sheet.

As described above with reference to FIG. 3, the tip end of the microneedle 12 is configured with the first outer edge 121 and the second outer edge 122 facing each other with the apex 123 of the microneedle 12 interposed therebetween. At step S12, the first outer edge 121 is formed but the second outer edge 122 is not formed. At this stage, therefore, the tip end of the microneedle 12 is not yet formed. That is, it can be said that step S12 (first incision step) is a step of forming the first outer edge 121 without forming the tip end of the microneedle 12.

At step S13, a second cut is made in a range from the first surface to the second surface of the sheet to form the second outer edge 122 that defines the tip end of the microneedle 12 (second incision step). That is, a second cut is made from the first surface to the second surface of the sheet to form the second outer edge 122. It should be noted that "to make a second cut in a range from the first surface to the second surface", that is, "to make a second cut from the first surface to the second surface" is not dependent on the direction of making a cut. The second cut therefore may be made from the first surface toward the second surface, or made from the second surface toward the first surface. The second cut passes through the sheet in the thickness direction, similarly to the first cut, and connects to the first cut.

This step S13 is performed after step S12. That is, the second outer edge 122 is formed after the first outer edge 121 is formed. At this stage, both of the first outer edge 121 and the second outer edge 122 are formed, and consequently, the tip end of the microneedle 12 is formed. A gap is produced by the first and second cuts around the tip end of the microneedle 12. As used herein, "to form the tip end of the microneedle" refers to forming the outer edge of the microneedle corresponding to the tip end.

At step S14, the sheet is cut to produce a plurality of microneedle sheets 10 from one sheet (cutting step). For example, the strip-shaped microneedle sheet 10 illustrated in FIG. 1 may be obtained by cutting the sheet processed at steps S11 to S13 along a machine direction and the width direction. Here, the machine direction is the feeding direction of the sheet in producing the microneedle sheet 10. The width direction is a direction orthogonal to both of the machine direction and the thickness direction of the sheet.

As described above, the microneedle may be defined with an additional outer edge different from both of the first outer edge and the second outer edge. The method of producing a microneedle sheet according to the present embodiment may therefore include a step for forming the additional outer edge, in addition to steps S11 to S14. In other words, the entire microneedle may be formed in two stages of steps S12 and S13 or may be formed by these two steps and one or more additional steps.

Step S14 (cutting step) is not essential. For example, when a sheet having a shape and a size of the microneedle sheet 10 at its completion is prepared at step S11 (preparation step), step S14 may be omitted.

In the method of producing a microneedle sheet according to the embodiment, it is not necessary to raise the microneedles 12 from the main surface 11a of the sheet body 11 in advance. The microneedle sheet 10 therefore can be produced readily and inexpensively.

Two kinds of cutting dies may be used for making cuts in a sheet in two stages. That is, a cutting die for making the first cut and a cutting die for making the second cut may be used. The cutting die refers to an article, a part, or a device having at least one cutting edge. FIG. 5 illustrates a first cutting die 21 and a second cutting die 22 that are an example of the two kinds of cutting dies. In the example in FIG. 5, the cross-sectional shape of a first cutting edge 211 and a second cutting edge 221 is substantially triangular. However, the shape of the cutting edge is not limited thereto and may be designed under any policy.

The first cutting die 21 includes one or more linear first cutting edges 211 arranged so as to be inclined by a predetermined angle relative to the machine direction MD. The second cutting die 22 includes one or more linear second cutting edges 221 arranged at a position corresponding to one or more first cutting edges 211. It can be said that the first cutting die 21 is a group of one or more first cutting edges 211 and the second cutting die 22 is a group of one or more second cutting edges 221. The inclination direction of the second cutting edge 221 is opposite to the inclination direction of the first cutting edge 211. For example, when the inclination angle of the first cutting edge 211 relative to the machine direction MD is +θ, the inclination angle of the second cutting edge 221 relative to the machine direction MD may be −θ. As used herein, the inclination angle of the cutting edge refers to the extending direction of the tip of the cutting edge in a state in which the extending direction is inclined relative to the machine direction. The inclination angle of the cutting edge refers to the angle formed between the extending direction of the tip of the cutting edge and the machine direction.

Since the cutting edge needs to pass through the sheet, the height of the cutting edge (the length from the base to the tip of the cutting edge) may be set in consideration of the thickness of the sheet. For example, the height of the cutting edge may be equal to or greater than the thickness of the sheet.

The material that forms the cutting edge is not limited. For example, a cutting edge made of stainless steel resistant to rust and having no effect on the active component may be used.

FIG. 6 illustrates an example of the method of producing the microneedle sheet 10 using the first cutting die 21 and the second cutting die 22. First of all, a sheet 1 is prepared (step S11), and subsequently, first cuts 31 are made in the sheet 1 using the first cutting die 21 to form first outer edges 121 (step S12). At this stage, only the linear first cuts 31 corresponding to the first cutting edges 211 are formed in the sheet 1, and the tip ends of the microneedles 12 are not formed. Subsequently, second cuts 32 are made in the sheet 1 using the second cutting die 22 to form second outer edges 122 (step S13). Only after this stage, the tip ends of the microneedles 12 are formed. Subsequently, the sheet 1 is cut, if necessary, to obtain the microneedle sheet 10 (step S14).

As illustrated in FIG. 6, at step S13 (second incision step), the second cut 32 may be made such that the second cut 32 intersects the first cut 31. The wording "the second cut intersects the first cut" refers to forming the second cut so as to cross a portion in the middle of the first cut. In this case, the first outer edge 121 and the second outer edge 122 are formed with the first cut 31 and the second cut 32 in the sheet body 11 of the microneedle sheet 10, and an X-shaped cut 33 is formed in the vicinity of the tip end of the microneedle 12. The second cut 32 is made so as to intersect the first cut 31, whereby the microneedle 12 having a sharp tip end can be formed reliably. For example, even when a small tip end angle of the microneedle 12 is set, a sharp microneedle 12 can be formed reliably.

The X-shaped cut 33 is not an essential constituent element of the microneedle sheet 10. The microneedles 12 having X-shaped cuts 33 in the vicinity of the tip ends and the microneedles 12 having no X-shaped cut 33 in the vicinity of the tip ends may be mixed in one microneedle sheet 10.

In the example in FIG. 6, the first cuts 31 are made using the first cutting die 21, and the second cuts 32 are made using the second cutting die 22. However, it should be noted that the relation of "first" and "second" between the cutting die and the cut is for the sake of convenience. Thus, the first cuts 31 may be made using the second cutting die 22, and the second cuts 32 may be made using the first cutting die 21.

[Modifications]

Figure 7:
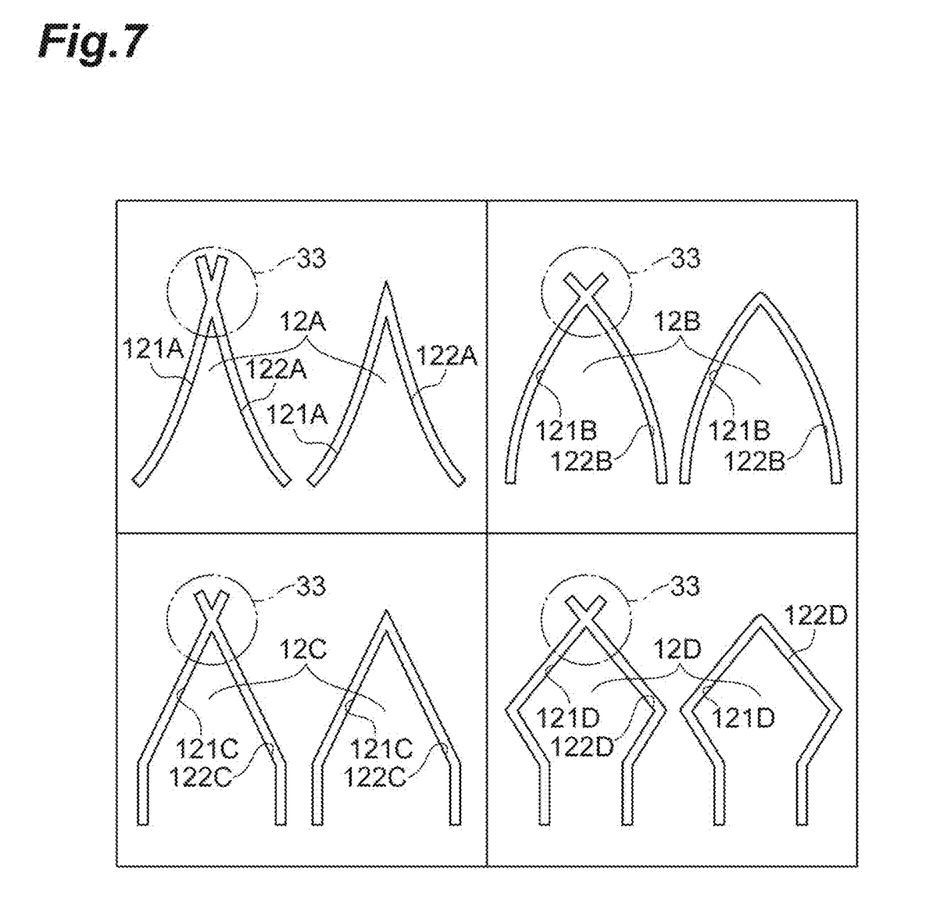
FIG. 7 is a diagram illustrating another example of microneedles.

As described above, the shape of the microneedle is not limited. For example, the microneedle may have a shape as illustrated in FIG. 7. FIG. 7 illustrates four kinds of shapes and illustrates, for each kind, a case where the X-shaped cut 33 is formed and a case where such a cut is not formed. The shape of a microneedle 12A is close to a triangle, but a first outer edge 121A and a second outer edge 122A have an arc shape protruding toward the inner side of the microneedle 12A. The shape of a microneedle 12B is also close to a triangle, but a first outer edge 121B and a second outer edge 122B have an arc shape protruding toward the outer side of the microneedle 12B. A microneedle 12C has such a shape that has a rectangular base and a triangular tip end in combination. A first outer edge 121C and a second outer edge 122C that define a tip end are linear. A microneedle 12D has such a shape that has a rectangular base and a rhombic tip end in combination. A first outer edge 121D and a second outer edge 122D that define the tip end side of the rhombic shape end are linear. In the examples in FIG. 3 and FIG. 7, the shape of the microneedle is line-symmetric, but the shape is not necessarily line-symmetric.

In the present embodiment, the microneedle sheet 10 is shaped like a strip. However, the shape of the microneedle sheet is not limited and, for example, may be a circle or an oval, may be other polygons such as an octagon, or may be a more complicated shape.

In the example in FIG. 6, the cutting die for making the first cuts and the cutting die for making the second cuts are separate. However, the first and second cuts may be made with one cutting die. For example, after the first cuts are made with a single cutting die, the sheet is rotated by the tip end angle of the microneedle. The second cuts are then made in the rotated sheet with the same cutting die to form the tip ends of the microneedles.

In the present embodiment, a cutting die is used for making the first cuts and the second cuts. However, the configuration of an article, a part, or a device for making these cuts is not limited. For example, a cutter other than a cutting die may be used, or laser light may be used.

In the present embodiment, each individual microneedle 12 is laid in a state in which the sheet body 11 is straight, and only after the sheet body 11 is bent, the microneedle 12 at the bent portion is raised. That is, the microneedles 12 formed by the production method according to the present embodiment are laid at a point of time when the microneedle sheet 10 is provided (that is, at a point of time before use). However, the microneedles formed by the production method according to the present embodiment may be raised from the main surface in a production step thereof. That is, the microneedles may be already raised from the main surface at a point of time when the microneedle sheet is provided.

Advantageous Effects

As described above, a method of producing a microneedle sheet according to an aspect of the present invention is a method of producing a microneedle sheet having at least one microneedle. The method includes: preparing a sheet having a first surface and a second surface; making a first cut in a range from the first surface to the second surface of the sheet to form a first outer edge that defines a tip end of the microneedle; and making, after forming the first outer edge, a second cut in a range from the first surface to the second surface of the sheet to form a second outer edge that defines the tip end of the microneedle, thereby forming the tip end of the microneedle.

In such an aspect, two outer edges (the first outer edge and the second outer edge) that define the tip end of the microneedle are not formed at one time but are formed separately by making cuts in a sheet in two stages. This technique can sharpen the tip end of the microneedle.

The inventors of the present invention have conducted elaborate studies on formation of microneedles and found that sharp microneedles can be formed by forming two outer edges that define the tip end of the microneedle, not at one time but separately. When a cut is made in one stage using a V-shaped cutting edge corresponding to the tip end of a microneedle, a microneedle having a chipped or rounded tip end tends to be formed. When a plurality of microneedles are formed in a sheet, some microneedles are sharp but other microneedles tend to have chipped or rounded tip ends. This tendency is conspicuous when the tip end angle of the microneedles is smaller. This means a microneedle sheet with poor quality. On the other hand, when cuts are made in a sheet in two stages, the number of microneedles having chipped or rounded tip ends is significantly reduced, and the quality of the microneedle sheet can be improved. For example, most, or almost all, or all of a plurality of microneedles provided to a microneedle sheet can be sharpened.

In the method of producing a microneedle sheet according to another aspect, the first outer edge may be an outer edge extending from an apex of the microneedle to a base of the microneedle, and the second outer edge may be an outer edge positioned on the opposite side to the first outer edge with the apex interposed and extending from the apex to the base. Since the apex of the microneedle is formed only after the second cut that is a cut in the second stage is made, the tip end of the microneedle can be sharpened.

In the method of producing a microneedle sheet according to another aspect, the making a first cut includes making the first cut with a first cutting die, and the making a second cut includes making the second cut with a second cutting die different from the first cutting die. Since the production process is simplified by using two kinds of cutting dies, the microneedle sheet can be produced at high speed. In addition, an article, a part, or a device used for production can be constructed inexpensively. Consequently, the production cost for the microneedle sheet can be suppressed.

In the method of producing a microneedle sheet according to another aspect, the first cutting die may be a group of linear first cutting edges, and the second cutting die may be a group of linear second cutting edges. Since the cutting edge for making a cut is linear, an article, a part, or a device used for producing the microneedle sheet can be constructed inexpensively. Consequently, the production cost for the microneedle sheet can be suppressed.

In the method of producing a microneedle sheet according to another aspect, the inclination angle of the first cutting edge relative to a machine direction may be $+\theta$, and the inclination angle of the second cutting edge relative to the machine direction may be $-\theta$. When the axis along the machine direction is taken as the axis of symmetry, the first cutting die and the second cutting die are disposed such that the inclinations of the first cutting edge and the second cutting edge are line-symmetric. Since the configuration of an article, a part, or a device for producing the microneedle sheet is simplified because of this arrangement, the production cost for the microneedle sheet can be suppressed, accordingly.

In the method of producing a microneedle sheet according to another aspect, the making a second cut includes making the second cut such that the second cut intersects the first cut. The second cut is made so as to cross a portion in the middle of the first cut, rather than making the second cut so as to connect to one end of the first cut, whereby the tip end of the microneedle can be sharpened more reliably.

In the method of producing a microneedle sheet according to another aspect, the making a second cut includes forming the tip end of the microneedle such that the tip end of the microneedle has a radius of curvature of 30 μm or less. The microneedle that punctures the skin reliably can be obtained by setting the radius of curvature in this way.

The inventors of the present invention have found that a microneedle having a tip end with a radius of curvature of 30 μm or less is unable to be stably fabricated when the tip end of the microneedle is formed by making a cut only one time rather than making a cut in two stages. One of the reasons for this is that it is difficult to prepare a V-shaped cutting edge for making a cut with a radius of curvature of 30 μm or less. It costs much to produce a V-shaped cutting edge for stably forming a cut with a radius of curvature of 30 μm or less, and there is a technical limitation in implementing the V-shaped cutting edge at low cost. Meanwhile, the inventors of the present invention have found that a sharp microneedle can be stably fabricated by making cuts in two stages, without involving special costs, even when the radius of curvature of the tip end is set to 30 μm or less.

In the method of producing a microneedle sheet according to another aspect, a plurality of microneedle sheets may be produced from the sheet by cutting the sheet after forming the tip end of the microneedle. The microneedle sheet can be produced efficiently by forming the outer shape of the microneedle sheet after forming the microneedle.

A microneedle sheet according to one aspect of the present invention includes a sheet body having a main surface, one or more microneedles formed in the sheet body, each microneedle having a tip end, and an X-shaped cut formed in the vicinity of the tip end of at least one microneedle among one or more microneedles.

If the X-shaped cut is formed in the vicinity of the tip end of at least some microneedles, it can be said that this microneedle sheet is fabricated by the method of producing a microneedle sheet according to an aspect of the present invention. The skin is therefore punctured reliably by the microneedle sheet having sharp microneedles.

In the microneedle sheet according to another aspect, in a first state in which the sheet body is not bent, the tip end of each of one or more microneedles may be oriented toward one end of the sheet body, and in a second state in which the sheet body is bent, among one or more microneedles, at least one microneedle positioned at a bent portion of the sheet body may be raised from the main surface. Since at least one microneedle is raised only after the sheet body is bent, the safety in handling the microneedles 12 can be ensured more reliably.

In the microneedle sheet according to another aspect, when returning from the second state to the first state, at least one microneedle having raised and the main surface may reduce an angle formed therebetween. Since at least one microneedle is raised only when the sheet body is bent, the safety in handling the microneedles 12 can be ensured more reliably.

In the microneedle sheet according to another aspect, the radius of curvature of the tip end of one or more microneedles may be 30 μm or less. The microneedle that punctures the skin reliably can be obtained by setting the radius of curvature in this way.

EXAMPLES

Although the present invention will be specifically described based on examples, the present invention is not limited thereto.

A PVA sheet was prepared, and a microneedle sheet according to an example was fabricated by making cuts in the sheet in two stages as described in the foregoing embodiment. For the design of each individual microneedle, the shape was triangular, the height (the length from the base to the tip end) was 500 μm, the tip end angle was 45°, and the radius of curvature was zero. The density of microneedles was 256 needles per cm². A support, an adhesive, and a liner were prepared, and a drug product was fabricated using these members and the fabricated microneedle sheet. This drug product was set in a dedicated applicator.

The applicator was moved on the fixed hairless rat skin to apply the drug product (microneedle sheet) to the skin, and immediately after application, the drug product was peeled off from the skin. The section having the drug product applied was dyed with Rhodamine, and an image of the applied section was captured by a fluorescence microscope (525 μm). Puncture marks of the microneedles were observed using the captured image, and the degree of uniformity in puncture was evaluated.

As a comparative example, a PVA sheet was prepared, and a microneedle sheet according to a comparative example was prepared by making a cut in the sheet in one stage using a cutting die that is a group of V-shaped cutting edges. For the design of each individual microneedle, the shape was triangular, the height (the length from the base to the tip end) was 500 μm, the tip end angle was 45°, and the radius of curvature was 30 μm. The density of microneedles was 256 needles per cm². A drug product was fabricated using this microneedle sheet by the same method as the example. The drug product was applied to the hairless rat skin, and the degree of uniformity in puncture was evaluated using a fluorescence microscope, in the same manner as in the example.

Figure 8:
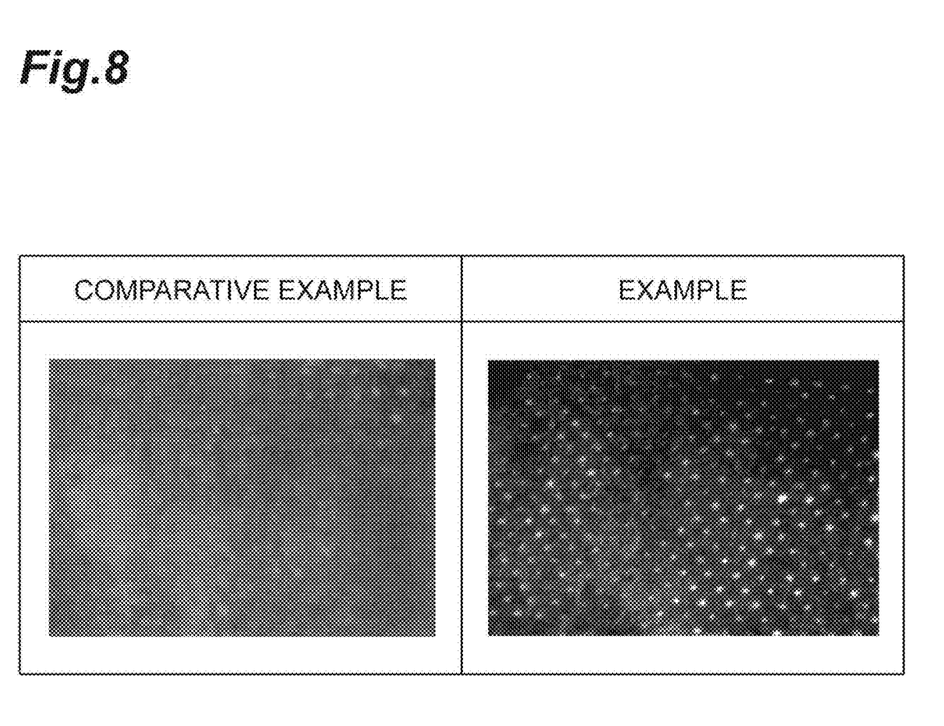
FIG. 8 is a diagram illustrating experiment results of puncture by microneedles.

The captured images obtained from the example and the comparative example are illustrated in FIG. 8. As is clear from this figure, the entire application range is punctured more reliably and the uniformity of puncture is obviously higher in the example than in the comparative example. This demonstrates that a plurality of sharp microneedles were stably fabricated successfully in the example, compared with the comparative example.

Experiments similar to that of the PVA sheet were conducted for a pullulan sheet and a PET sheet. For these two kinds of sheets, the uniformity of puncture was increased by making cuts in the sheet in two stages to form a microneedle, rather than by a method of making a cut in one stage.

The present invention has been described in detail above based on the embodiments and examples thereof. However, the present invention is not limited by the foregoing embodiments. The present invention is susceptible to various modifications without departing from the spirit of the invention.

REFERENCE SIGNS LIST

1 . . . sheet, 10 . . . microneedle sheet, 11 . . . sheet body, 11a . . . main surface, 12, 12A, 12B, 12C, 12D . . . microneedle, 121, 121A, 121B, 121C, 121D . . . first outer edge, 122, 122A, 122B, 122C, 122D . . . second outer edge, 123 . . . apex, 124 . . . base, S1 . . . first state, S2 . . . second state, 21 . . . first cutting die, 22 . . . second cutting die, 211 . . . first cutting edge, 221 . . . second cutting edge, MD . . . machine direction, 31 . . . first cut, 32 . . . second cut, 33 . . . X-shaped cut.

The invention claimed is:

1. A method of producing a microneedle sheet having at least one microneedle, the method comprising:
preparing a sheet having a first surface and a second surface;
making a first cut in a range from the first surface to the second surface of the sheet to form a first outer edge of a tip end of the microneedle; and
making, after forming the first outer edge, a second cut in a range from the first surface to the second surface of the sheet to form a second outer edge of the tip end of the microneedle, thereby forming the tip end of the microneedle;
wherein the first outer edge is an outer edge extending from an apex of the microneedle to a base of the microneedle, and wherein the second outer edge is an outer edge positioned on an opposite side to the first outer edge with the apex interposed and extending from the apex toward the base.

2. The method of producing a microneedle sheet according to claim 1, wherein
the making a first cut includes making the first cut with a first cutting die, and
the making a second cut includes making the second cut with a second cutting die different from the first cutting die.

3. The method of producing a microneedle sheet according to claim 2, wherein
the first cutting die is a group of linear first cutting edges, and
the second cutting die is a group of linear second cutting edges.

4. The method of producing a microneedle sheet according to claim 3, wherein
an inclination angle of the first cutting edge relative to a machine direction is $+\Theta$, and
an inclination angle of the second cutting edge relative to the machine direction is $-\Theta$.

5. The method of producing a microneedle sheet according to any one of claim 1, wherein the making a second cut includes making the second cut such that the second cut intersects the first cut.

6. The method of producing a microneedle sheet according to any one of claim 1, wherein the making a second cut includes forming the tip end of the microneedle such that the tip end of the microneedle has a radius of curvature of 30 mm or less.

7. The method of producing a microneedle sheet according to any one of claim 1, further comprising cutting, after forming the tip end of the microneedle, the sheet to generate a plurality of the microneedle sheets from the sheet.

* * * * *